(12) United States Patent
McColl et al.

(10) Patent No.: US 9,261,477 B2
(45) Date of Patent: Feb. 16, 2016

(54) HEMATOCRIT CORRECTED GLUCOSE MEASUREMENTS FOR ELECTROCHEMICAL TEST STRIP USING TIME DIFFERENTIAL OF THE SIGNALS

(75) Inventors: David McColl, Inverness (GB); Mandip Farmahan, Inverness (GB); Antony Smith, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 159 days.

(21) Appl. No.: 13/261,835

(22) PCT Filed: Aug. 31, 2012

(86) PCT No.: PCT/EP2012/067028
§ 371 (c)(1),
(2), (4) Date: Mar. 28, 2014

(87) PCT Pub. No.: WO2013/030375
PCT Pub. Date: Mar. 7, 2013

(65) Prior Publication Data
US 2014/0216948 A1    Aug. 7, 2014

Related U.S. Application Data

(60) Provisional application No. 61/530,795, filed on Sep. 2, 2011.

(51) Int. Cl.
*G01N 27/327* (2006.01)

(52) U.S. Cl.
CPC ............................. *G01N 27/3274* (2013.01)

(58) Field of Classification Search
None
See application file for complete search history.

(56) References Cited

U.S. PATENT DOCUMENTS

2010/0170807 A1*  7/2010  Diebold et al. .... G01N 27/3274
                                                          205/792
2011/0139634 A1   6/2011  Chou et al.

FOREIGN PATENT DOCUMENTS

| EP | 1394545 A1 | 3/2004 |
|---|---|---|
| WO | 2006070200 | 7/2006 |
| WO | 2011/082820 A1 | 7/2011 |

OTHER PUBLICATIONS

International Search Report and the Written Opinion of the International Searching Authority, PCT/EP2012/067028; Date of mailing—Dec. 5, 2012.

* cited by examiner

*Primary Examiner* — J. Christopher Ball

(57) ABSTRACT

Various embodiments that allow for determination of hematocrit by a time differential between the input and output signals such that a glucose measurement for a blood sample can be corrected by the measured hematocrit of the blood sample.

5 Claims, 9 Drawing Sheets

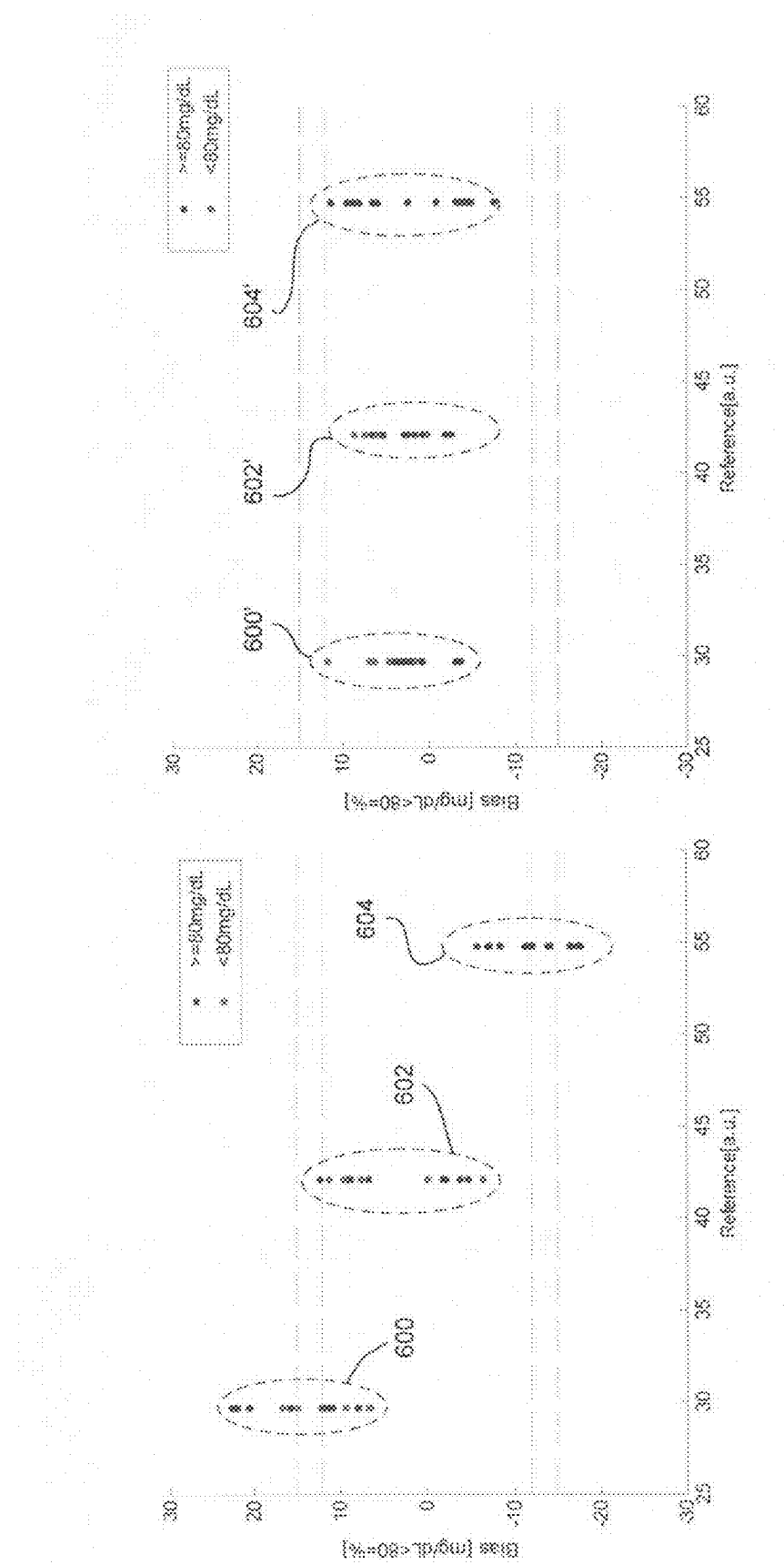

HEMATOCRIT CORRECTED GLUCOSE MEASUREMENTS FOR ELECTROCHEMICAL TEST STRIP USING TIME DIFFERENTIAL OF THE SIGNALS

PRIORITY

This application claims the benefits of priority under 35 USC §119, 120, 365 and 371 of prior filed U.S. Provisional Patent Application Ser. No. 61/530,795 filed on Sep. 2, 2011, and International Patent Application PCT/EP2012/067028 filed on Aug. 31, 2012, which applications are incorporated by reference in their entirety hereinto this application as if fully set forth herein.

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.

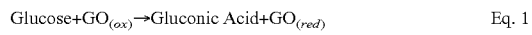

$$\text{Glucose} + GO_{(ox)} \rightarrow \text{Gluconic Acid} + GO_{(red)} \qquad \text{Eq. 1}$$

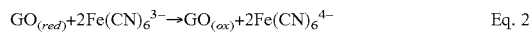

$$GO_{(red)} + 2Fe(CN)_6^{3-} \rightarrow GO_{(ox)} + 2Fe(CN)_6^{4-} \qquad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These sensors have certain disadvantages.

SUMMARY OF THE DISCLOSURE

Applicants have discovered various embodiments of a technique to allow for improved glucose measurement using a time differential of the input and output signals to an electrochemical biosensor chamber.

In one aspect, a method to determine a glucose concentration in a blood sample is provided. The method can be achieved by: depositing a blood sample in a test chamber of a test strip having at least first and second electrodes in contact with a reagent and third and fourth electrodes not in contact with the reagent; driving a non-oscillating signal to the at least first and second electrodes to cause a reaction with the glucose in the blood sample and the reagent; measuring a current output of the reaction to establish a preliminary glucose concentration; applying a first oscillating input signal at a first frequency to third and fourth electrodes; detecting a first oscillating output signal from the third and fourth electrodes; measuring a first time differential between the first input and output oscillating signals; applying a second oscillating input signal at a second frequency to the third and fourth electrodes; detecting a second oscillating output signal from the third and fourth electrodes; measuring a second time differential between the first input and output oscillating signals; estimating a hematocrit of the blood sample based on the first and second time differentials; and deriving a final glucose concentration based on the preliminary glucose concentration and the hematocrit from the estimating step. In a variation of this method, a first frequency may be about 25,000 Hertz and the second frequency may be about 100 kiloHertz to 1 Mega- Hertz, and preferably about 250 kilo Hertz and the estimating may include applying an equation of the form:

$$HCT_{EST} = \frac{(C_1 \Delta t_1 - C_2 \Delta t_2 - C_3)}{m_1}$$

where each of $C_1$, $C_2$, and $C_3$ may include an operational constant for the test strip, and are based on manufacturing parameters depending on the design of the strip.

In another variation, the measuring of a current output for the preliminary glucose concentration is performed prior to the estimating of the hematocrit. In yet a further variation, a deriving may include calculating the final glucose concentration $G_F$ from:

$$G_F = \frac{\left(\frac{I_E}{1 - k(HCT_{EST} - h_0)}\right) - c_3}{m_3}$$

where $I_E$ may include a magnitude of the measured end current; $HCT_{EST}$ may include the hematocrit; h0 may include nominal hematocrit, and k, m3 and $c_3$ comprise parameters from regressions data.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 6A illustrates glucose measurements that are not corrected to demonstrate the bias (vertical axis) against the hematocrit level (horizontal axis) of those measurements.

FIG. 6B illustrates the glucose measurements that have been corrected to demonstrate the improvement in bias (vertical axis) against the hematocrit level (horizontal axis).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional.

Figure 1:
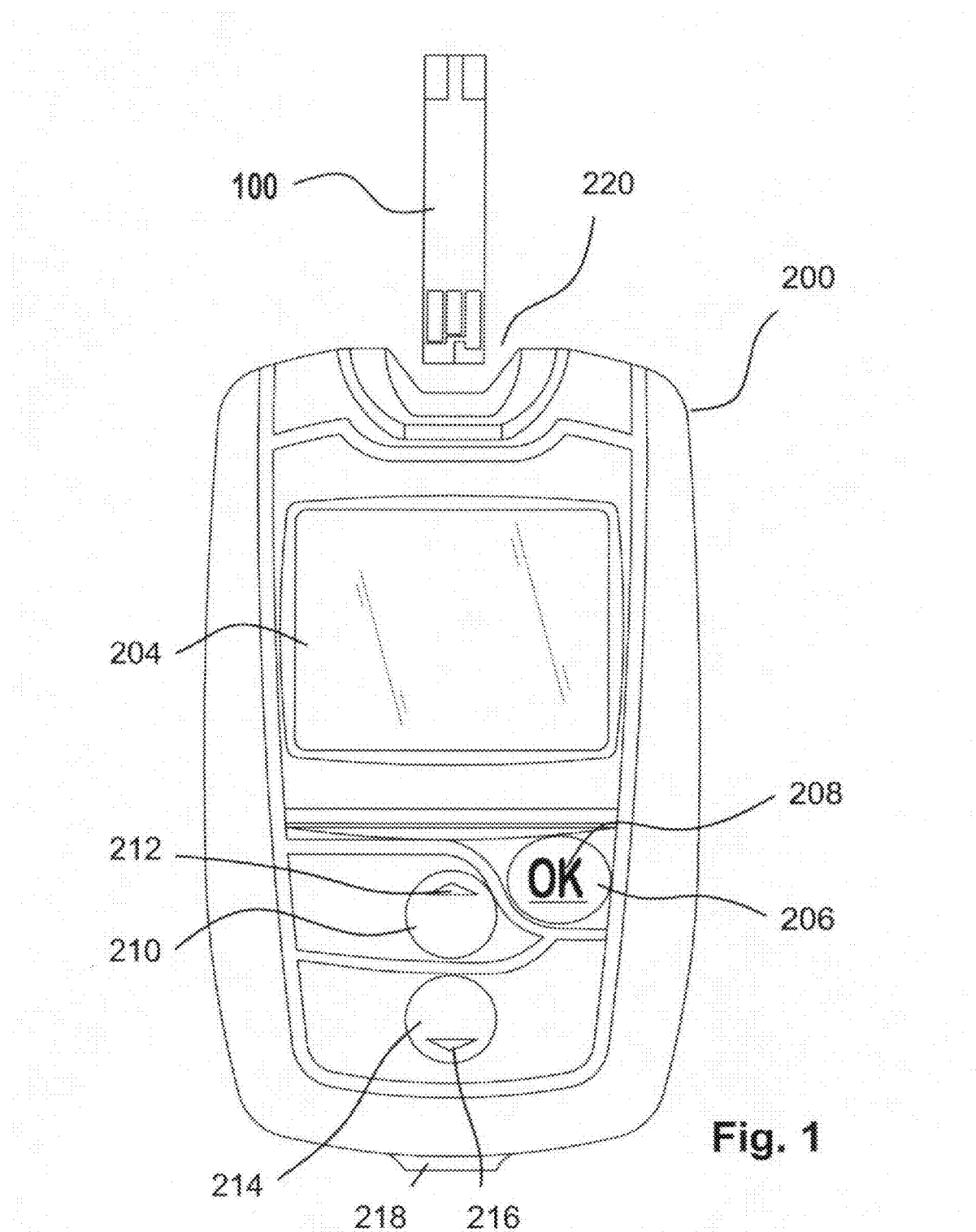
FIG. 1 illustrates an analyte measurement system.

FIG. 1 illustrates a test meter 200, for testing glucose levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 into a strip port connector 220, by pressing and briefly holding first user interface input 206, or by the detection of data traffic across a data port 218. Test meter 200 can be switched off by removing test strip 100, pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2:
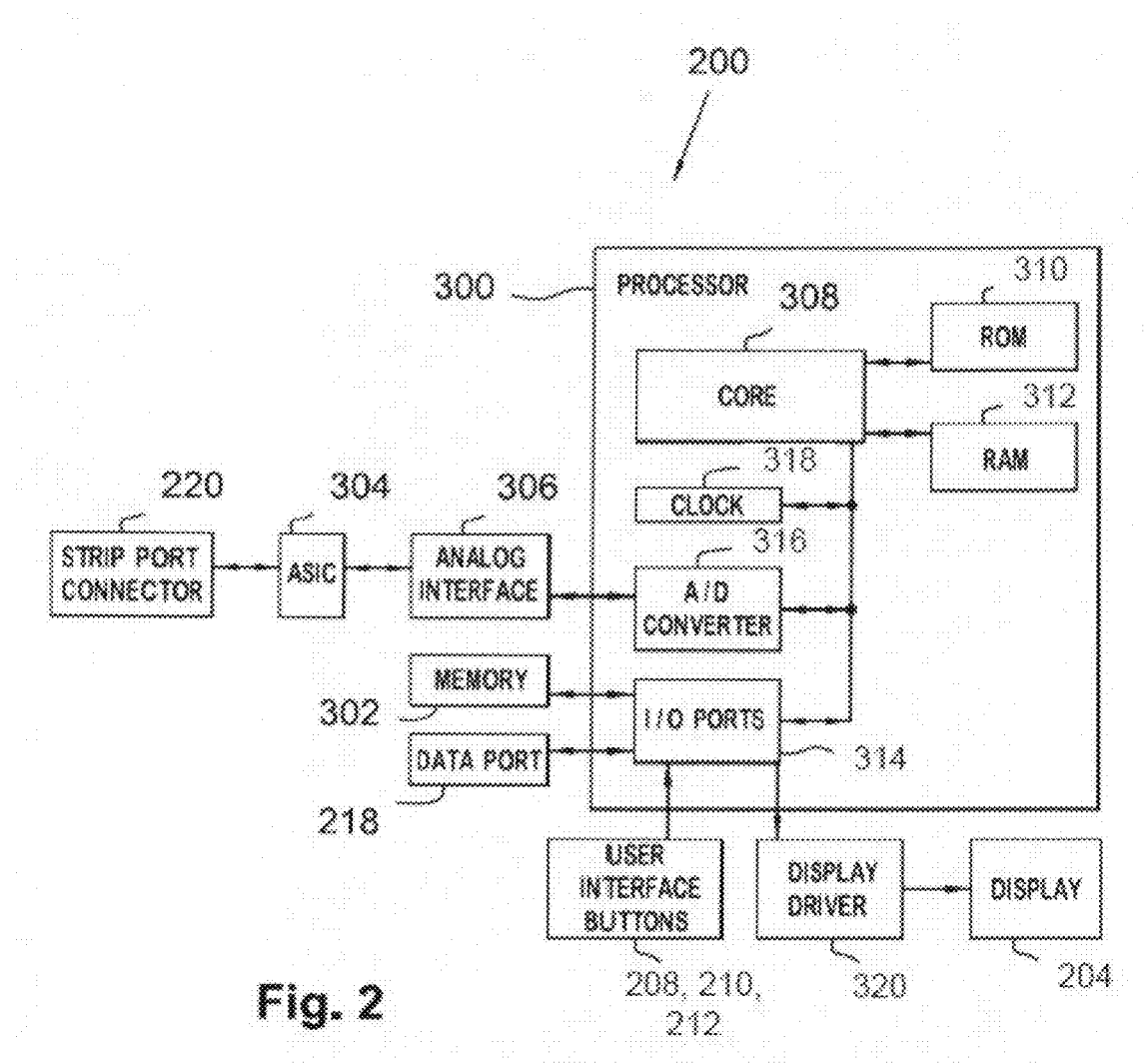
FIG. 2 illustrates in simplified schematic form the components of the meter 200.

Referring to FIG. 2, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein, with a copy attached hereto the appendix.

Figure 3A:
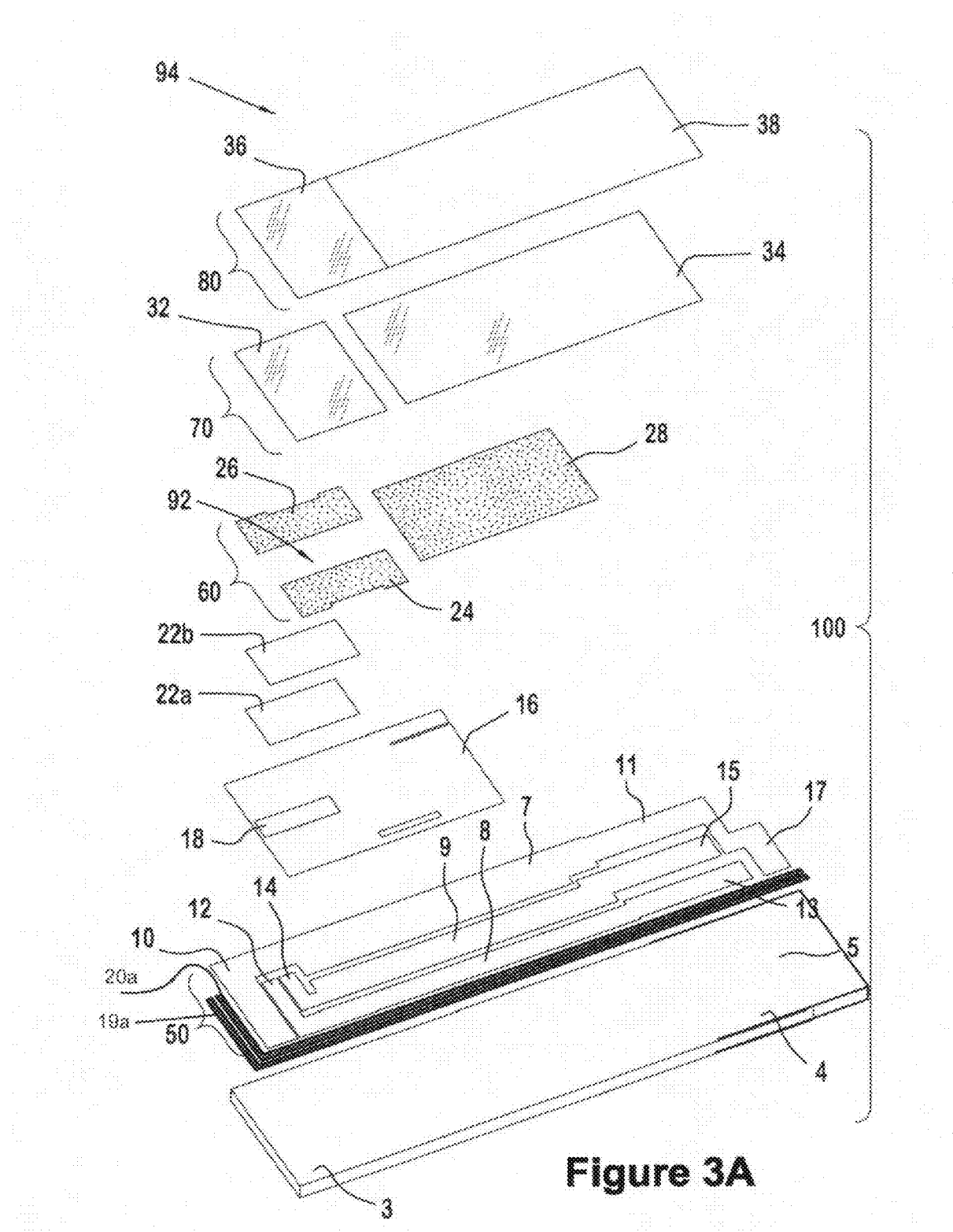
FIG. 3A illustrates the test strip 100 of the system of FIG. 1 in which there are two correction electrodes upstream of the measurement electrodes.

FIG. 3A is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the correction electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Test strip 100 may include a sample-receiving chamber 92 through which a blood sample may be drawn. Sample-receiving chamber 92 can include an inlet at a proximal end and an outlet at the side edges of test strip 100, as illustrated in FIG. 3A. A blood sample 94 can be applied to the inlet to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A. For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, first conductive layer 50 may include a reference electrode 10, a first working electrode 12, a second working electrode 14, third and fourth correction electrodes 19a and 19b, a first contact pad 13, a second contact pad 15, a reference contact pad 11, a first working electrode track 8, a second working electrode track 9, a reference electrode track 7, and a strip detection bar 17. The correction electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A.

Figures 3B, 3C:
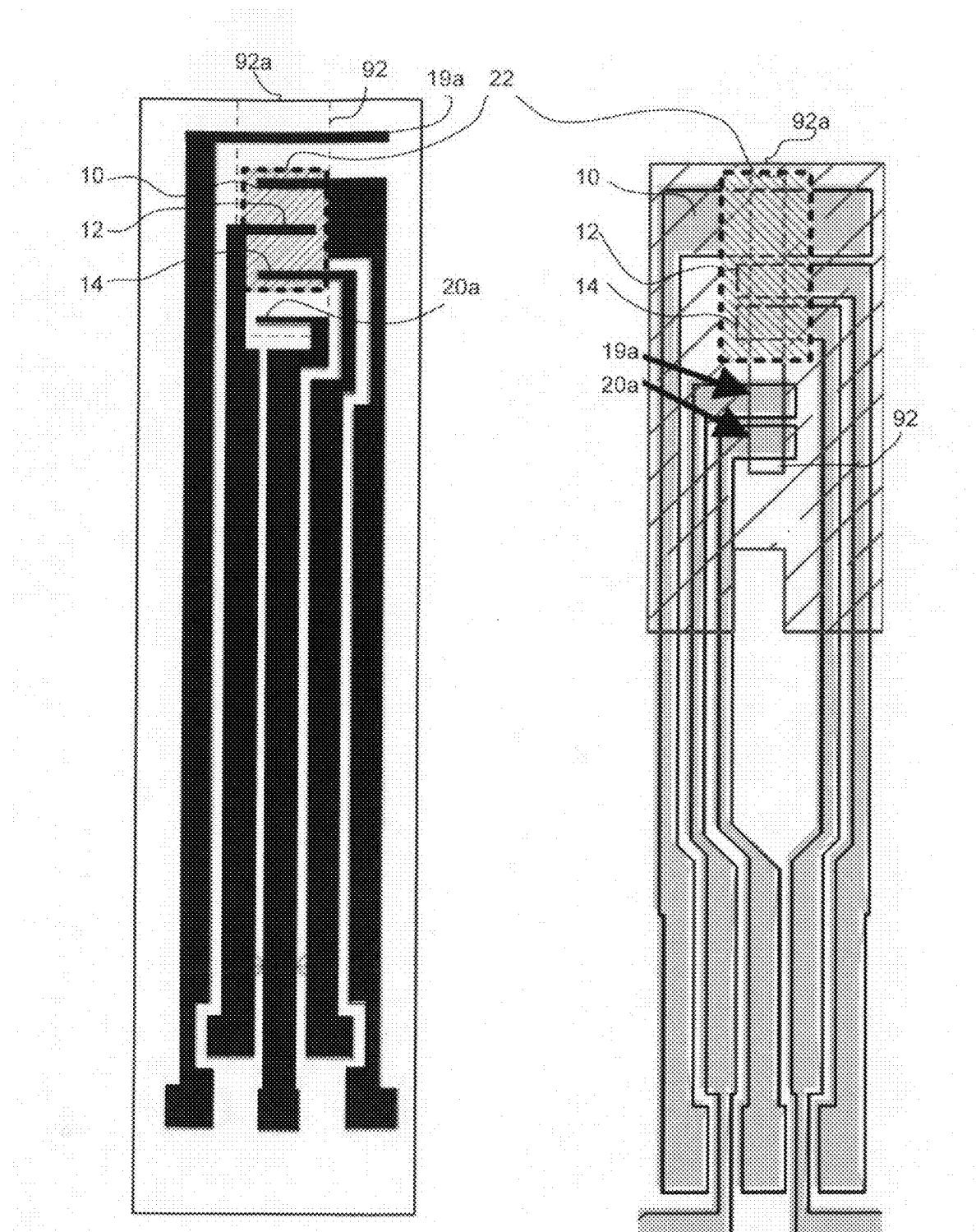
FIG. 3B illustrates a variation of the test strip of FIG. 3A in which one measurement electrode is disposed proximate the entrance and the other measurement electrode is at the terminal end of the test cell with the measurement electrodes disposed between the pair of correction electrodes.
FIGS. 3C and 3D illustrate variations of FIG. 3A in which the correction electrodes are disposed next to each other at the terminal end of the test chamber with the measurement electrodes upstream of the correction electrodes.
Figures 3D, 3E:
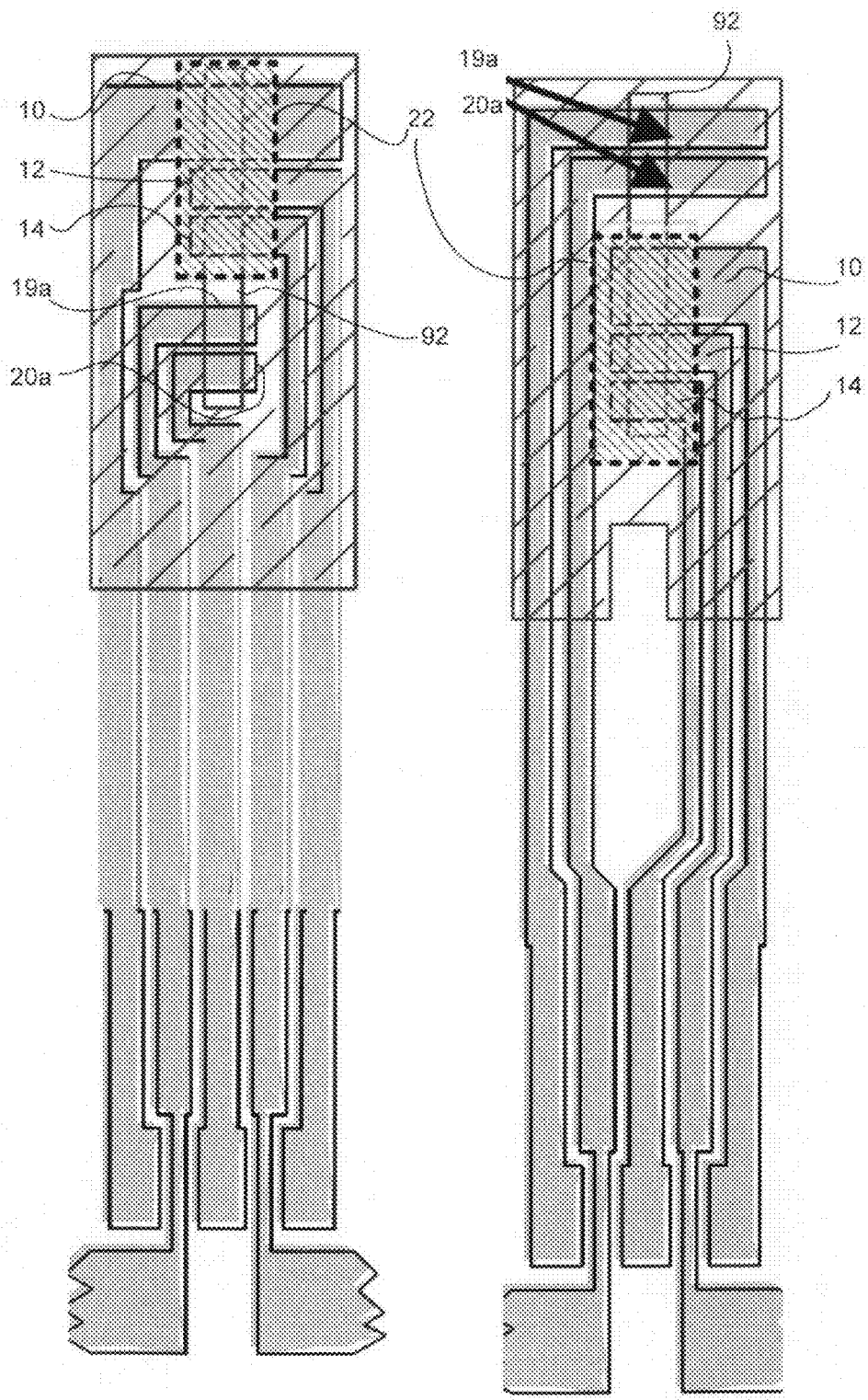
FIGS. 3E and 3F illustrates a correction electrodes arrangement similar to that of FIG. 3A in which the pair of correction electrodes are proximate the entrance of the test chamber.
Figure 3F:
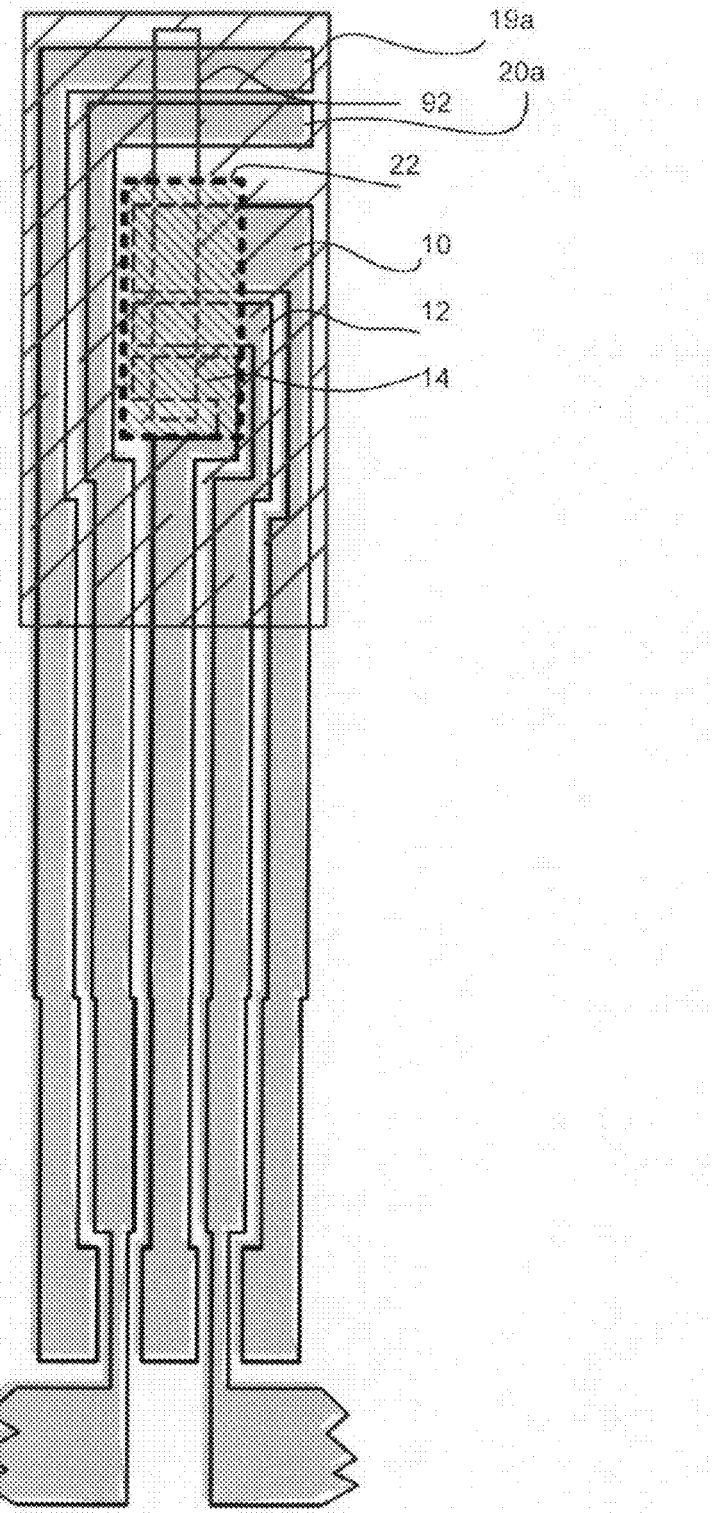

Variations of the test strip 100 (FIG. 3A) are shown in FIGS. 3B, 3C, 3D, 3E, and 3F. In the embodiment of FIG. 3B, the analyte measurement electrodes 10, 12, and 14 are disposed in generally the same configuration as in FIG. 3A. The electrodes 19a and 20a to sense hematocrit level, however, are disposed in a spaced apart configuration in which one electrode 19a is proximate an entrance 92a to the test chamber 92 and another electrode 20a is at the opposite end of the test chamber 92. Electrodes 10, 12, and 14 are disposed to be in contact with a reagent layer 22. In FIGS. 3C, 3D, and 3E, the hematocrit sensing electrodes 19a and 20a are disposed adjacent each other and may be placed at the opposite end 92b of the entrance 92a to the test chamber 92 (FIGS. 3C and 3D) or adjacent the entrance 92a (FIGS. 3E and 3F). In all of these embodiments, the correction electrodes are spaced apart from the reagent layer 22 so that these correction electrodes are not impacted by the electrochemical reaction of the reagent in the presence of a fluid sample (e.g., blood or interstitial fluid) containing glucose.

In the various embodiments of the test strip, there are two measurements that are made to a blood sample deposited on the test strip. One measurement is that of the glucose in the blood sample while the other is that of hematocrit in the same sample. The measurement of the hematocrit is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the hematocrit; the hematocrit measurement first then the glucose measurement; both measurements at the same time; or a duration of one measurement may overlap a duration of the other measurement. Each measurement is discussed in detail as follow with respect to FIGS. 4 and 5.

Figure 4A:
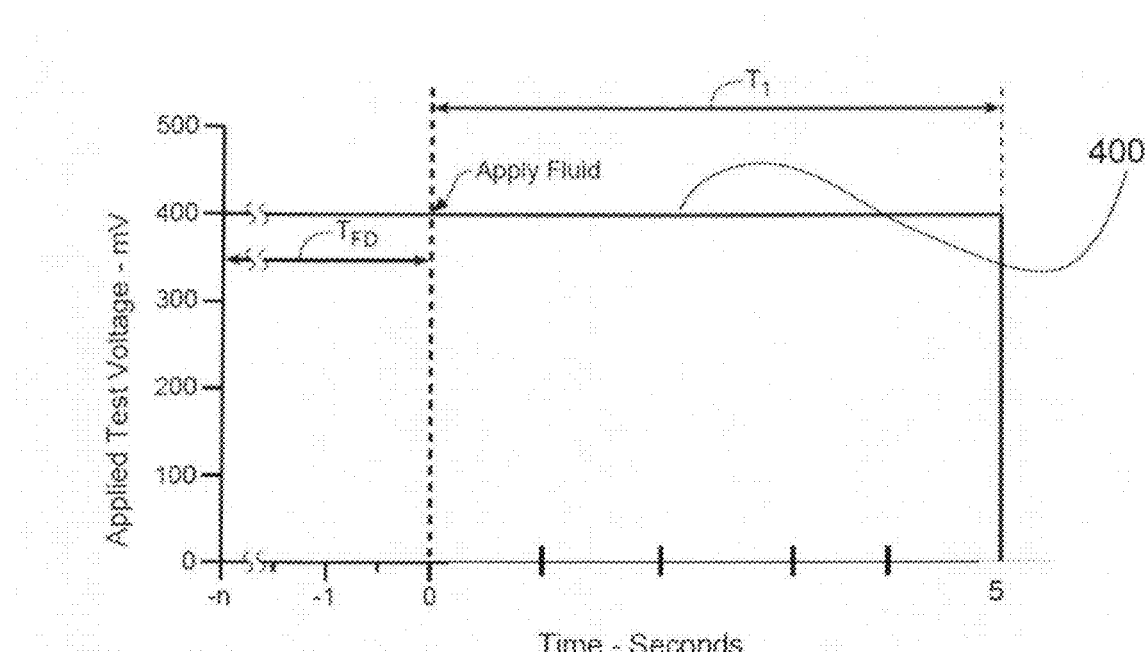
FIG. 4A illustrates a graph of time over applied potential to the test strip of FIG. 1.

FIG. 4A is an exemplary chart of a test voltage applied to test strip 100 and its variations shown here in FIGS. 3A-3F. Before a fluid sample is applied to test strip 100, test meter 200 is in a fluid detection mode in which a first test voltage of about 400 millivolts is applied between second working electrode 14 and reference electrode 10. A second test voltage of about 400 millivolts is preferably applied simultaneously between first working electrode 12 and reference electrode 10. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at starting time at zero. In the fluid detection mode, test meter 200 determines when a fluid is applied to test strip 100 such that the fluid wets second working electrode 14 and reference electrode 10. Once test meter 200 recognizes that the physiological fluid has been applied because of, for example, a sufficient increase in the measured test current at second working electrode 14, test meter 200 assigns a zero second marker at zero time "0" and starts the test time interval $T_1$. Upon the completion of the test time interval $T_1$, the test voltage is removed. For simplicity, FIG. 4A only shows the first test voltage applied to test strip 100.

Hereafter, a description of how glucose concentration is determined from the known current transients (i.e., the measured electrical current response in nanoamperes as a function of time) that are measured when the test voltages of FIG. 4A are applied to the known test strip 100.

In FIG. 4A, the first and second test voltages applied to test strip 100 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $T_1$ is measured relative to time $t_0$. As the voltage 400 is maintained in FIG. 4A for the duration of T1, the current transient 402 for the first working electrode is generated starting at zero time and likewise the current transient 404 for the second working electrode is also generated with respect to the zero time. The current transients build up to a peak proximate peak time Tp at which time, the current slowly drops off until approximately 5 seconds after zero time. At the point 406, the current value for each of the working electrodes are measured and added together. From knowledge of the calibration code offset and slope for the particular test strip 100, the glucose concentration can be calculated. "Intercept" and "Slope" are the values obtained by measuring calibration data from a batch of test strips. Typically around 1500 strips are selected at random from the lot or batch. Body fluid from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current), A graph of measured glucose concentration is plotted against actual glucose concentration (or measured current versus YSI current), and a formula y=mx+c least squares fitted to the graph to give a value for batch slope m and batch intercept c for the remaining strips from the lot or batch.

Figure 4B:
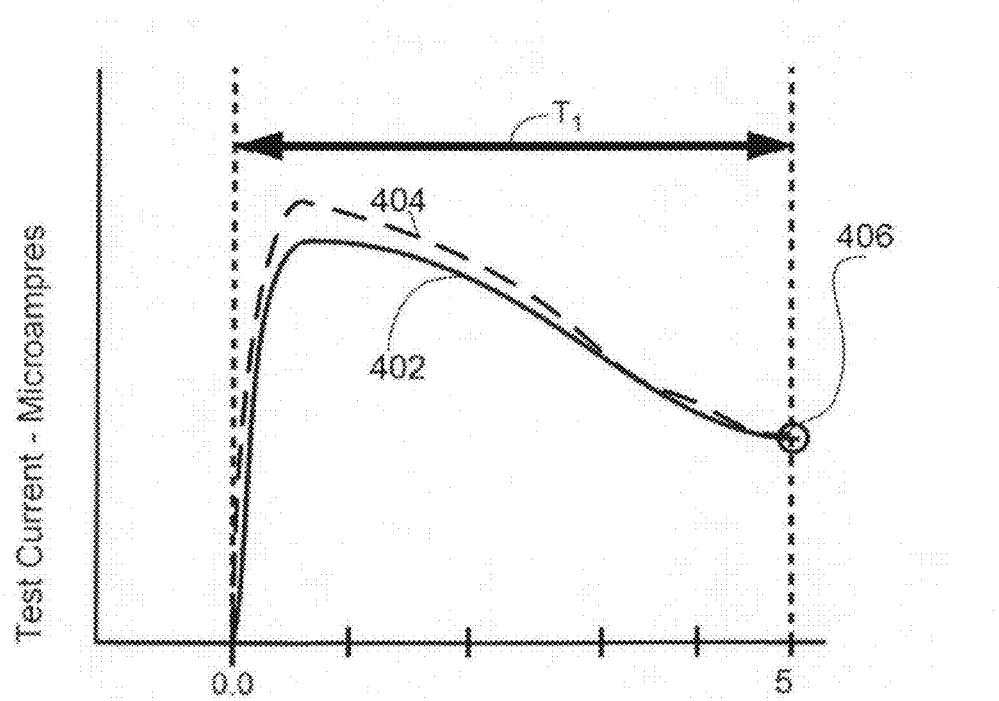
FIG. 4B illustrates a graph of time over output current from the test strip of FIG. 1.

As an example of an analyte calculation (e.g., glucose) for strip 100 (FIG. 3A), it is assumed in FIG. 4B that the sampled current value at 406 for the first working electrode is 1600 nanoamps whereas the current value at 406 for the second working electrode is 1300 nanoamps and for the calibration code of the test strip the Intercept is 500 nanoamps and the Slope is 18 nanoamp/mg/dL. Glucose concentration $G_0$ can be thereafter be determined from Equation 3 as follow:

$$G_0 = [(I_E) - \text{Intercept}]/\text{Slope} \qquad \text{Eq. 3}$$

where $I_E$ is a preliminary glucose concentration determined from the sum of the end currents measured at both electrodes or $I_{we1} + I_{we2}$ $I_{we1}$ is the current measured for the first working electrode at the end of T1;

$I_{we2}$ is the current measured for the second working electrode at the end of T1;

Slope is the value obtained from calibration testing of a batch of test strip of which this particular strip comes from;

Intercept is the value obtained from calibration testing of a batch of test strip of which this particular strip comes from.

From Eq. 3 $G_0=[(1600+1300)-500]/18$ and therefore, $G_0=133.33$ nanoamp~133 mg/dL.

It is noted that the glucose concentration here is not corrected for any hematocrit value and that certain offsets may be provided to the current value $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Figure 5:
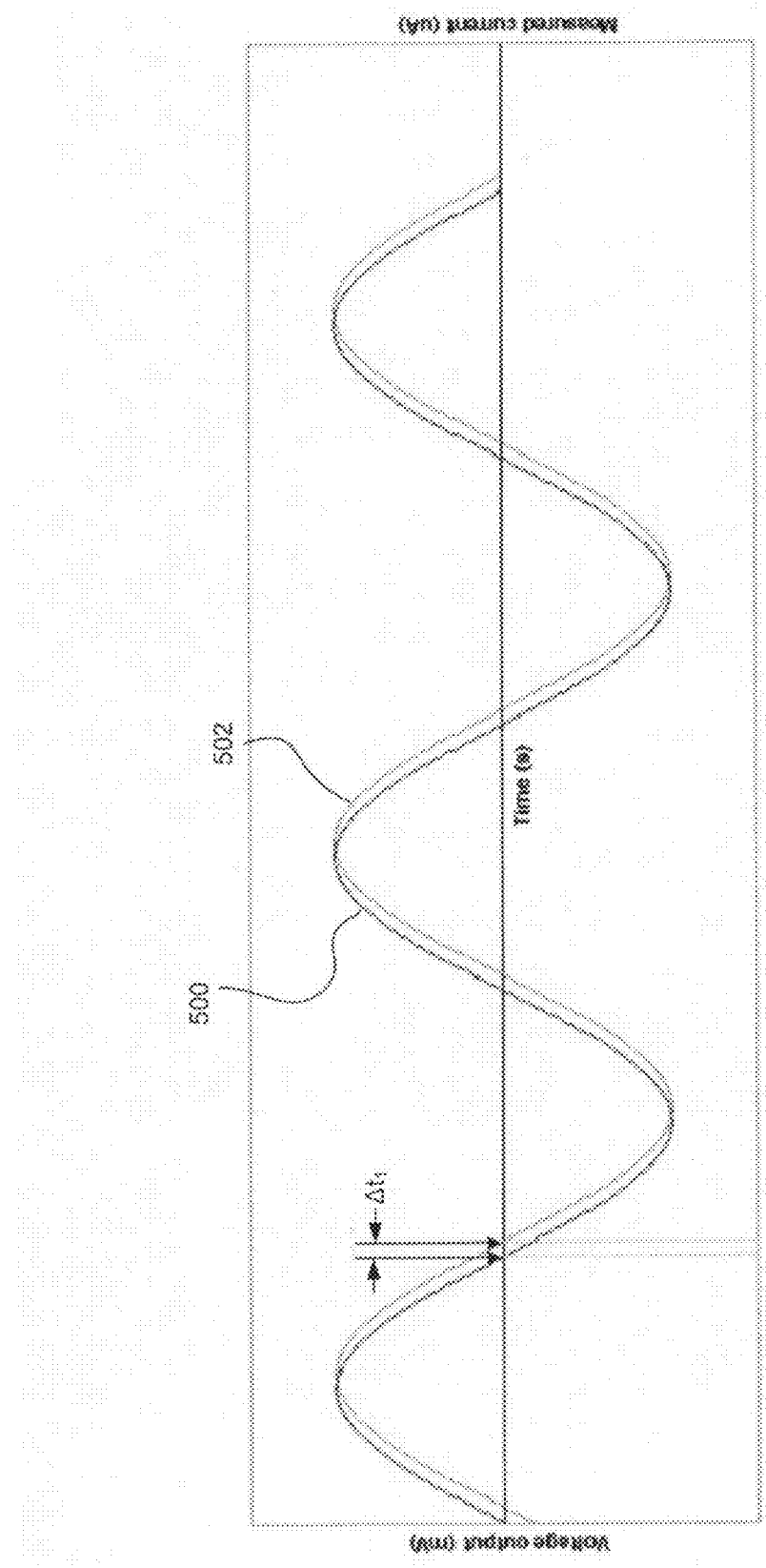
FIG. 5 illustrates a waveform applied to the test chamber and a waveform as measured from the test chamber to show a time delay between the waveforms.

Now that a preliminary glucose concentration ($I_E$) can be determined from the end currents, a description of applicant's technique to determine the hematocrit of the blood sample is provided in relation to FIG. 5. In FIG. 5, the system 200 (FIG. 2) applies a first oscillating input signal 500 at a first frequency (of about 25,000 Hertz) to a pair of electrodes. The system is also set up to measure or detect a first oscillating output signal 502 from the third and fourth electrodes, which in particular involve measuring a first time differential $\Delta t_1$ between the first input and output oscillating signals. At the same time or during overlapping time durations, the system may also apply a second oscillating input signal (not shown for brevity) at a second frequency (about 100 kiloHertz to 1 MegaHertz, and preferably about 250 kilo Hertz) to a pair of electrodes and then measure or detect a second oscillating output signal from the third and fourth electrodes, which may involve measuring a second time differential $\Delta t_2$ (not shown) between the first input and output oscillating signals. From these signals, the system estimate a hematocrit of the blood sample based on the first and second time differentials $\Delta t_1$ and $\Delta t_2$. Thereafter, the system is able to derive a final glucose concentration based on the preliminary glucose concentration and the estimate of the hematocrit. The estimate can be done by applying an equation of the form $$HCT_{EST} = \frac{(C_1 \Delta t_1 - C_2 \Delta t_2 - C_3)}{m_1} \quad \text{Eq. 4}$$

Where each of $C_1$, $C_2$, and $C_3$ is an operational constant for the test strip.

And the derivation include calculating the final glucose concentration $G_F$ from Equation 5 of the form:

$$G_F = \frac{\left(\frac{I_E}{1-k(HCT_{EST}-h_0)}\right)-c_4}{m_3} \quad \text{Eq. 5}$$

Where $I_E$ represents a preliminary glucose concentration $HCT_{EST}$ represents the hematocrit, $h_0$ represents nominal hematocrit, and k, $m_3$ and $c_4$ represent parameters from regressions data.

It is noted that in the preferred embodiments, the measure of a current output for the preliminary glucose concentration is performed prior to the estimation of the hematocrit. Alternatively, the hematocrit level can be estimated prior to the measurement of the preliminary glucose concentration. In either case, the preliminary glucose measurement $I_E$ is obtained by Equation 3 and the hematocrit estimation is obtained by Equation 4 and the corrected or final glucose measurement $G_F$ is obtained by using estimated hematocrit and the preliminary glucose concentration in the form of Equation 5. Details of the technique to correct a glucose estimation with hematocrit correction is provided in International Published Application WO 2008/040998 published on Apr. 10, 2008 entitled "Systems and Methods for Determining a Substantially Hematocrit Independent Analyte Concentration," which application is incorporated by reference and attached hereto the Appendix.

For this technique, experiments were performed to quantify the improvement in the glucose measurements that have been corrected as compared to glucose measurements that have not been corrected. The quantification of the improvement can be shown by the "bias" at different levels of hematocrit. The bias, which is an estimate of the relative error in the glucose measurement, was calculated for each glucose concentration determined with the method described in this example. The bias for each glucose concentration was determined with equations of the form:

$Bias_{abs} = G_{calculated} - G_{reference}$ for $G_{reference}$ less than 80 mg/dL glucose and $$Bias_\% = \frac{G_{calculated} - G_{reference}}{G_{reference}}$$

for $G_{reference}$ greater than or equal to 80 mg/dL glucose where $Bias_{abs}$ is absolute bias, $Bias_\%$ is percent bias, $G_{calculated}$ is the glucose concentration determined by the method herein and $G_{reference}$ is the reference glucose concentration.

In this example, (number of strip samples 226) of the measurements were made at glucose concentrations of less than 80 mg/dL and at concentrations greater than 80 mg/dL. The hematocrit levels of these samples were parsed into three main ranges at 30%, 42% and 55% hematocrit. As can be seen in FIG. 6A, the glucose measurements 600 and 604 had greater absolute bias (from 8-25%) at the low hematocrit (~30%) and at high (~55%) hematocrit than as compared to the glucose measurements 602 at the middle (~42%) level of hematocrit where the bias is within the range of −5% to +12%. In contrast, as can be seen in FIG. 6B, the bias of glucose measurements 600', 602' and 604' are now within the range of ±12% at the corresponding hematocrit levels (30%, 42% and 55%) as in the uncorrected measurements of FIG. 6A.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method to determine a glucose concentration in a blood sample, the method comprising:

depositing a blood sample in a test chamber of a test strip having at least first and second electrodes in contact with a reagent and third and fourth electrodes not in contact with the reagent;

driving a non-oscillating signal to the at least first and second electrodes to cause a reaction with the glucose in the blood sample and the reagent;

measuring a current output of the reaction to establish a preliminary glucose concentration;

applying a first oscillating input signal at a first frequency to third and fourth electrodes;

detecting a first oscillating output signal from the third and fourth electrodes;

measuring a first time differential between the first input and output oscillating signals;

applying a second oscillating input signal at a second frequency to the third and fourth electrodes;

detecting a second oscillating output signal from the third and fourth electrodes;

measuring a second time differential between the first input and output oscillating signals;

estimating a hematocrit of the blood sample based on the first and second time differentials; and deriving a final glucose concentration based on the preliminary glucose concentration and the hematocrit from the estimating step.

2. The method of claim 1, in which the first frequency comprises about 25,000 Hertz and the second frequency comprises about 250,000 Hertz.

3. The method of claim 2, in which the estimating comprises applying an equation of the form $$HCT_{EST} = \frac{(C_1 \Delta t_1 - C_2 \Delta t_2 - C_3)}{m_1}$$

Where each of $C_1$, $C_2$, and $C_3$ comprises an operational constant for the test strip.

4. The method of claim 3, in which the measuring of a current output for the preliminary glucose concentration is performed prior to the estimating of the hematocrit.

5. The method of claim 3, in which the deriving comprises calculating the final glucose concentration $G_F$ from:

$$G_F = \frac{\left(\frac{I_E}{1 - k(HCT_{EST} - h_0)}\right) - c_3}{m_3}$$

where $I_E$ comprises a magnitude of the measured end current $HCT_{EST}$ comprises the hematocrit, $h_0$ comprises nominal hematocrit, and k, $m_3$ and $c_3$ comprise parameters from regression data.

* * * * *